United States Patent
Locke et al.

(10) Patent No.: US 9,138,515 B2
(45) Date of Patent: Sep. 22, 2015

(54) SYSTEM AND METHOD FOR MANAGING REDUCED PRESSURE AT A TISSUE SITE

(71) Applicant: KCI Licensing, Inc., San Antonio, TX (US)

(72) Inventors: Christopher Brian Locke, Bournemouth (GB); Mark Stephen James Beard, Ferndown (GB)

(73) Assignee: KCI Licensing, Inc., San Antonio, TX (US)

( * ) Notice: Subject to any disclaimer, the term of this patent is extended or adjusted under 35 U.S.C. 154(b) by 162 days.

(21) Appl. No.: 13/780,438

(22) Filed: Feb. 28, 2013

(65) Prior Publication Data

US 2013/0172839 A1      Jul. 4, 2013

Related U.S. Application Data (62) Division of application No. 12/069,364, filed on Feb. 8, 2008, now Pat. No. 8,409,170.

(60) Provisional application No. 60/900,556, filed on Feb. 9, 2007.

(51) Int. Cl.
*A61M 1/00* (2006.01)

(52) U.S. Cl.
CPC .......... *A61M 1/0031* (2013.01); *A61M 1/0027* (2014.02); *A61M 1/0088* (2013.01); *A61M 2205/15* (2013.01); *A61M 2205/3344* (2013.01); *A61M 2205/583* (2013.01)

(58) Field of Classification Search
CPC ............ A61M 1/0027; A61M 1/0031; A61M 2205/15; A61M 2205/3344
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Susan Su (57) ABSTRACT

The illustrative embodiments described herein are directed to an apparatus and method for managing reduced pressure at a tissue site. The apparatus includes a reduced pressure source that generates reduced pressure. The reduced pressure is delivered to the tissue site via a delivery tube. The apparatus includes a single pressure sensor. The single pressure sensor detects an actual reduced pressure at the tissue site. The apparatus also includes a controller. The controller determines a responsiveness of the actual reduced pressure measured by the single pressure sensor to an increase in reduced pressure generated by the reduced pressure source. The apparatus includes an indicator. The indicator emits a signal when the controller determines that the actual reduced pressure measured by the single pressure sensor is nonresponsive to the increase in reduced pressure generated by the reduced pressure source.

12 Claims, 6 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0040687 A1 | 2/2003 | Boynton |
| 2004/0006319 A1* | 1/2004 | Lina et al. ............... 604/304 |
| 2006/0025727 A1 | 2/2006 | Boehringer |
| 2007/0032763 A1 | 2/2007 | Vogel |
| 2007/0219489 A1* | 9/2007 | Johnson et al. ........... 604/96.01 |
| 2008/0009815 A1* | 1/2008 | Grabenkort et al. ........ 604/346 |
| 2008/0103440 A1* | 5/2008 | Ferren et al. ............. 604/95.01 |
| 2009/0264837 A1* | 10/2009 | Adahan .................. 604/290 |
| 2010/0042074 A1* | 2/2010 | Weston et al. ............. 604/543 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| JP | W02007030599 | 3/2007 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 00/21586 A1 | 4/2000 |
| WO | 00/61206 | 10/2000 |
| WO | 03/018098 A2 | 3/2003 |
| WO | 2006/114648 A2 | 11/2006 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Bjorn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N. A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

SYSTEM AND METHOD FOR MANAGING REDUCED PRESSURE AT A TISSUE SITE

CROSS-REFERENCE TO RELATED APPLICATIONS

This application is a Divisional of U.S. application Ser. No. 12/069,364 filed Feb. 8, 2008, which claims the benefit of U.S. Provisional Application No. 60/900,556, filed Feb. 9, 2007, which is hereby incorporated by reference.

BACKGROUND OF THE INVENTION

1. Field of the Invention

The present invention relates generally to the field of tissue treatment, and more specifically to a system and method for applying reduced pressure at a tissue site.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. The treatment of wounds using reduced pressure is sometimes referred to in the medical community as "negative pressure tissue treatment," "reduced pressure therapy," or "vacuum therapy." This type of treatment provides a number of benefits, including faster healing, and increased formulation of granulation tissue.

The reduced pressure at a tissue site caused by a reduced pressure treatment system may need to be properly managed to maintain or increase the effectiveness of the reduced pressure treatment. In addition, leaks and blockages in the components of the reduced pressure treatment system may need to be detected and corrected to maintain effective treatment. For example, a leak or blockage in the tube that connects a reduced pressure source, such as a vacuum pump, to the tissue site may disrupt the reduced pressure treatment being administered to the tissue site. The management or control of reduced pressure treatment systems may be generally referred to as "pump pressure control" or "differential pressure control."

In one currently used pump pressure control system, pressure is measured at the pump outlet and fed into a control system that drives a pump to achieve a target pressure at the outlet of the pump. However, the system neglects any differential between the pressure measured at the pump outlet and the pressure in proximity to the tissue site because pressure is not measured at or near the tissue site. Thus, this currently used pump pressure control system fails to provide information about leaks or blockages that occur between the tissue site and the pump.

Currently used differential pressure control systems employ two sensors to measure pressure at both the pump outlet and at the tissue site. The pressures measured by the two sensors are compared so that the occurrence of leaks or blockages in reduced pressure treatment system may be identified. However, the two sensors used by current differential pressure control systems increase the systems' size, weight, cost, and complexity. For example, the use of two sensors increases the amount of electronic circuitry and power used by the reduced pressure treatment system. In addition, comparing measurements from two different sensors requires that the reduced pressure treatment system include circuitry and software for making the comparison. The additional components required by current differential pressure control systems reduce those systems' ability to be used to treat low-severity wounds and wounds on ambulatory patients. In addition, the additional components increase the obtrusiveness and weight of the reduced pressure treatment system, thereby increasing the discomfort and limiting the mobility of the patient.

BRIEF SUMMARY OF THE INVENTION

To alleviate the existing problems with reduced pressure treatment systems, the illustrative embodiments described herein are directed to an apparatus and method for managing reduced pressure at a tissue site. The apparatus includes a reduced pressure source that generates reduced pressure. The reduced pressure is delivered to the tissue site via a delivery tube. The apparatus includes a single pressure sensor. The single pressure sensor detects an actual reduced pressure at the tissue site. The apparatus also includes a controller. The controller determines a responsiveness of the actual reduced pressure measured by the single pressure sensor to an increase in reduced pressure generated by the reduced pressure source. The apparatus includes an indicator. The indicator emits a signal when the controller determines that the actual reduced pressure measured by the single pressure sensor is nonresponsive to the increase in reduced pressure generated by the reduced pressure source.

The illustrative embodiments also provide a method for managing reduced pressure at a tissue site. The process determines a target reduced pressure. The process detects an actual reduced pressure at the tissue site using a single pressure sensor. The process compares the actual reduced pressure with the target reduced pressure to form a comparison. The process performs a reduced pressure management function based on the comparison.

In another embodiment, the process increases a generated reduced pressure using a reduced pressure source. The process determines an actual reduced pressure at the tissue site using a single pressure sensor. The process emits a signal using an indicator in response to the actual reduced pressure at the tissue site being nonresponsive to increasing the generated reduced pressure.

DETAILED DESCRIPTION OF THE PREFERRED EMBODIMENT

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The illustrative embodiments described herein provide and apparatus and method for managing reduced pressure at a tissue site. Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

The apparatus includes a reduced pressure source that generates reduced pressure. A reduced pressure source is any device capable of generating reduced pressure. The reduced pressure is delivered to the tissue site via a delivery tube. The apparatus includes a single pressure sensor. A pressure sensor is any device capable of measuring or detecting a pressure. The single pressure sensor detects an actual reduced pressure at the tissue site. In one embodiment, the single pressure sensor is the only pressure sensor included in the apparatus.

The apparatus also includes a controller. A controller is any device capable of processing data, such as data from the single pressure sensor. A controller may also control the operation of one or more components of the apparatus. The controller determines a responsiveness of the actual reduced pressure measured by the single pressure sensor to an increase in reduced pressure generated by the reduced pressure source.

In one embodiment, the reduced pressure source generates a decreased reduced pressure when the actual reduced pressure at the tissue site detected by the single pressure sensor exceeds a target reduced pressure. In another embodiment, the reduced pressure source generates an increased reduced pressure when a target reduced pressure exceeds the actual reduced pressure at the tissue site detected by the single pressure sensor.

The apparatus may also include a relief valve coupled to the delivery tube. A relief valve is any valve capable of decreasing the reduced pressure. In this embodiment, the relief valve may open to decrease the actual reduced pressure at the tissue site when the actual reduced pressure at the tissue site detected by the single pressure sensor exceeds a target reduced pressure by a predetermined threshold.

As used herein, the term "coupled" includes coupling via a separate object. For example, the relief valve may be coupled to the delivery tube if both the relief valve and the relief tube are coupled to a third object. The term "coupled" also includes "directly coupled," in which case the two objects touch each other in some way. The term "coupled" also encompasses two or more components that are continuous with one another by virtue of each of the components being formed from the same piece of material.

The apparatus includes an indicator. An indicator is any device capable of emitting a signal. For example, the indicator may emit a signal to a user of the apparatus. The indicator emits a signal when the controller determines that the actual reduced pressure measured by the single pressure sensor is nonresponsive to the increase in reduced pressure generated by the reduced pressure source. "Nonresponsive" may refer to the lack of an effect on the actual reduced pressure, as measured by the single pressure sensor, from an increase in reduced pressure generated by the reduced pressure source. Additional details regarding the responsiveness of the actual reduced pressure measured by the single pressure sensor are provided in the illustrative embodiments described below.

The illustrative embodiments also provide a method for managing reduced pressure at a tissue site. The process determines a target reduced pressure. The target reduced pressure may be any reduced pressure that is set by a user or the apparatus, such as the controller. The process detects an actual reduced pressure at the tissue site using a single pressure sensor. The process compares the actual reduced pressure with the target reduced pressure to form a comparison. The process performs a reduced pressure management function based on the comparison. A reduced pressure management function is any operation, function, or activity of any or all of the components of the apparatus. For example, a reduced pressure management function may be performed by one or more components of the apparatus. A reduced pressure management function may also be performed by a user.

In one embodiment, performing the reduced pressure management function based on the comparison includes decreasing a generated reduced pressure generated by a reduced pressure source in response to the actual reduced pressure exceeding the target reduced pressure. In another embodiment, the process opens a relief valve that decreases the actual reduced pressure at the tissue site in response to the actual reduced pressure exceeding the target reduced pressure by a predetermined threshold. In another embodiment, the process eliminates the generated reduced pressure by turning off the reduced pressure source in response to the actual reduced pressure exceeding the target reduced pressure by a predetermined threshold.

In another embodiment, performing the reduced pressure management function based on the comparison includes increasing a generated reduced pressure generated by a reduced pressure source in response to the target reduced pressure exceeding the actual reduced pressure. In this embodiment, the process may emit a signal using an indicator in response to the actual reduced pressure at the tissue site being nonresponsive to increasing the generated reduced pressure.

In one example, the actual reduced pressure at the tissue site is nonresponsive to increasing the generated reduced pressure when the actual reduced pressure at the tissue site fails to increase within a predefined time period in response to increasing the generated reduced pressure. In another example, the actual reduced pressure at the tissue site is nonresponsive to increasing the generated reduced pressure when the actual reduced pressure at the tissue site fails to meet a target reduced pressure within a predefined time period in response to increasing the generated reduced pressure. In a specific non-limiting example, the predefined time period may be in a range of 4 to 6 seconds.

Figure 1:
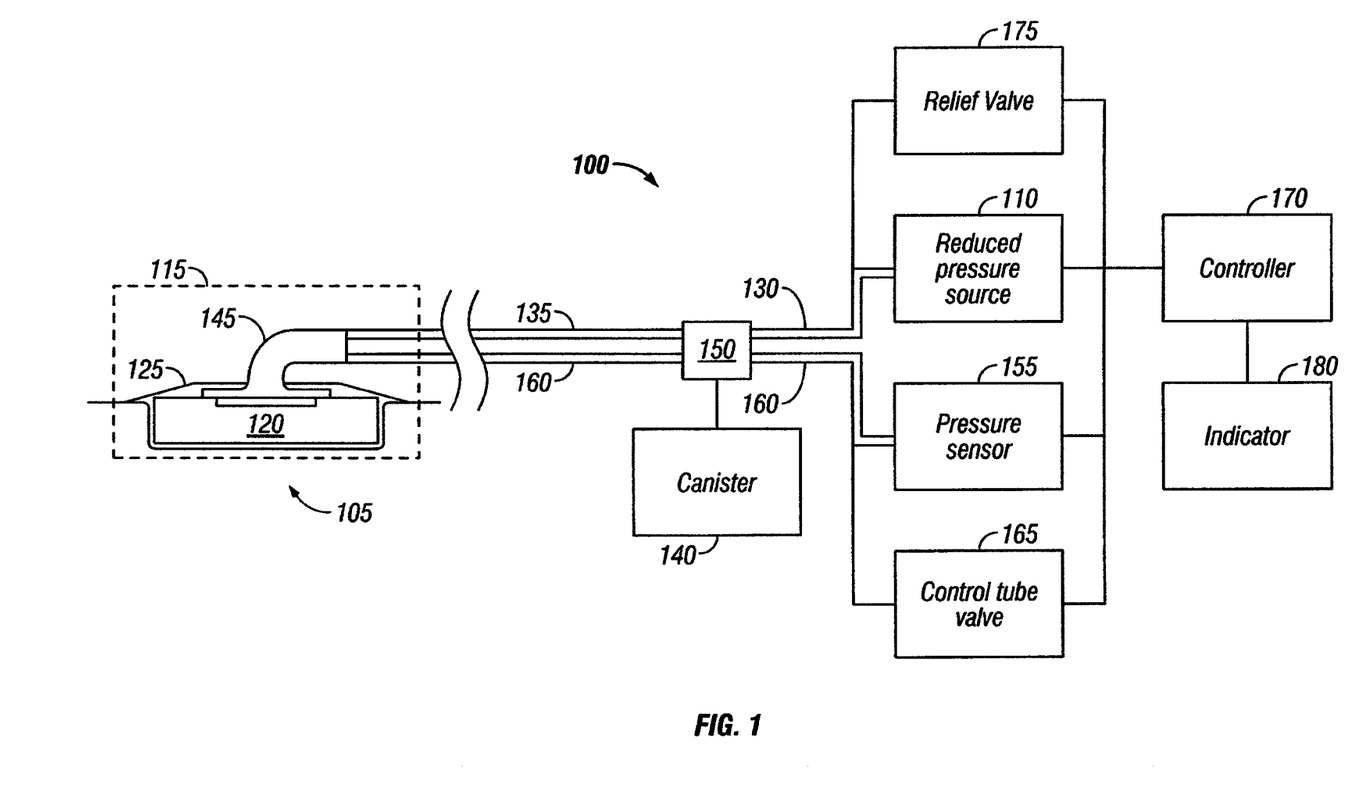
FIG. 1 is a block diagram of an apparatus for managing reduced pressure at a tissue site in accordance with an illustrative embodiment of the present invention.

Turning now to FIG. 1, a block diagram of an apparatus for managing reduced pressure at a tissue site is depicted in accordance with an illustrative embodiment of the present invention. Specifically, FIG. 1 shows reduced pressure treatment system 100 for managing the reduced pressure to tissue site 105.

Reduced pressure treatment system 100 may be used to apply reduced pressure treatment to tissue site 105. Tissue site 105 may be the bodily tissue of any human, animal, or other organism, including bone tissue, adipose tissue, muscle tissue, dermal tissue, vascular tissue, connective tissue, cartilage, tendons, ligaments, or any other tissue. While tissue site 105 may include a wound, diseased tissue, or defective tissue, the tissue site may further include healthy tissue that is not wounded, diseased, or defective. The application of reduced pressure to tissue site 105 may be used to promote the drainage of exudate and other liquids from tissue site 105, as well as promote the growth of additional tissue. In the case in which tissue site 105 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location.

The reduced pressure that is applied to tissue site 105 is generated by reduced pressure source 110. Reduced pressure source 110 may be any type of manually, mechanically, or electrically operated pump. Non-limiting examples of reduced pressure source 110 include devices that are driven by stored energy, and which are capable of producing a reduced pressure. Examples of these stored energy, reduced pressure sources include, without limitation, pumps driven by piezo electric energy, spring energy, solar energy, kinetic energy, energy stored in capacitors, combustion, and energy developed by Sterling or similar cycles. Other examples of reduced pressure source 110 include devices that are manually activated, such as bellows pumps, peristaltic pumps, diaphragm pumps, rotary vane pumps, linear piston pumps, pneumatic pumps, hydraulic pumps, hand pumps, foot pumps, and manual pumps such as those used with manually-activated spray bottles. Still other devices and processes that may be used or included in reduced pressure source 110 include syringes, lead screws, ratchets, clockwork-driven devices, pendulum-driven devices, manual generators, osmotic processes, thermal heating processes, and processes in which vacuum pressures are generated by condensation.

In another embodiment, reduced pressure source 110 may include a pump that is driven by a chemical reaction. A tablet, solution, spray, or other delivery mechanism may be delivered to the pump and used to initiate the chemical reaction. The heat generated by the chemical reaction may be used to drive the pump to produce the reduced pressure. In another embodiment, a pressurized gas cylinder such as a CO2 cylinder is used to drive a pump to produce the reduced pressure. In still another embodiment, reduced pressure source 110 may be a battery-driven pump. Preferably, the pump uses low amounts of power and is capable of operating for an extended period of time on a single charge of the battery.

Reduced pressure source 110 provides reduced pressure to tissue site 105 via dressing 115. Dressing 115 includes manifold 120, which may be placed to adjacent to or in contact with tissue site 105. Manifold 120 may be a biocompatible, porous material that is capable of being placed in contact with tissue site 105 and distributing reduced pressure to the tissue site 105. Manifold 120 may be made from foam, gauze, felted mat, or any other material suited to a particular biological application. Manifold 120 may include a plurality of flow channels or pathways to facilitate distribution of reduced pressure or fluids to or from tissue site 105.

In one embodiment, manifold 120 is a porous foam and includes a plurality of interconnected cells or pores that act as flow channels. The porous foam may be a polyurethane, open-cell, reticulated foam such as GranuFoam manufactured by Kinetic Concepts, Inc. of San Antonio, Tex. If an open-cell foam is used, the porosity may vary, but is preferably about 400 to 600 microns. The flow channels allow fluid communication throughout the portion of manifold 120 having open cells. The cells and flow channels may be uniform in shape and size, or may include patterned or random variations in shape and size. Variations in shape and size of the cells of manifold result in variations in the flow channels, and such characteristics may be used to alter the flow characteristics of fluid through manifold 120.

In one embodiment, manifold 120 may further include portions that include "closed cells." These closed-cell portions of manifold 120 contain a plurality of cells, the majority of which are not fluidly connected to adjacent cells. Closed-cell portions may be selectively disposed in manifold 120 to prevent transmission of fluids through perimeter surfaces of manifold 120.

Manifold 120 may also be constructed from bioresorbable materials that do not have to be removed from a patient's body following use of reduced pressure treatment system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. Manifold 120 may further serve as a scaffold for new cell-growth, or a scaffold material may be used in conjunction with manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In one example, the scaffold material has a high void-fraction (i.e. a high content of air).

In other embodiments, the manifold 120 may be formed from porous hydrogels or hyrogel-forming materials, textiles, such as fabrics, ceramics, laminates, biologics, biopolymers, corks, and hemostatic dressings. Alternatively, beads may be placed in contact with the tissue site 105 and used to distribute reduced pressure.

Dressing 115 also includes sealing member 125. Manifold 120 may be secured to tissue site 105 using sealing member 125. Sealing member 125 may be a cover that is used to secure manifold 120 at tissue site 105. While sealing member 125 may be impermeable or semi-permeable, in one example sealing member 125 is capable of maintaining a reduced pressure at tissue site 105 after installation of the sealing member 125 over manifold 120. Sealing member 125 may be a flexible drape or film made from a silicone based compound, acrylic, hydrogel or hydrogel-forming material, or any other biocompatible material that includes the impermeability or permeability characteristics desired for tissue site 105. Sealing member 125 may be formed of a hydrophobic material to prevent moisture absorption by the sealing member 125.

Instead of being provided in "sheet" form such as that of a drape, sealing member 125 may be provided in a pourable or sprayable form that is applied over the manifold 120 after placement of manifold 120 in contact with the tissue site 105. Similarly, sealing member 125 may include a device that is placed over manifold 120 and tissue site 105 to provide sealing functionality, including but not limited to a suction cup, a molded cast, and a bell jar.

In one embodiment, sealing member 125 is configured to provide a sealed connection with the tissue surrounding manifold 120 and tissue site 105. The sealed connection may be provided by an adhesive positioned along a perimeter of sealing member 125 or on any portion of sealing member 125 to secure sealing member 125 to manifold 120 or the tissue surrounding tissue site 105. The adhesive may be pre-positioned on sealing member 125 or may be sprayed or otherwise applied to sealing member 125 immediately prior to installing sealing member 125.

As an alternative to an adhesive sealant, a sealed connection may be provided by circumferentially wrapping the area adjacent to tissue site 105 with sealing member 125. For example if tissue site 105 is located on an extremity of a patient, an elongated drape or "drape tape" could be wrapped multiple times around manifold 120 and the area surrounding tissue site 105 to provide the sealed connection. Alternatively, the sealed connection between, sealing member 125 and the tissue surrounding tissue site 105 may be provided by reduced pressure applied by reduced pressure treatment system 100. In this embodiment, the perimeter of sealing member 125 could be "vacuum" sealed to a patient's skin. In still another embodiment, sealing member 125 may be sutured to the tissue surrounding tissue site 105 to provide a sealed connection.

In some cases, sealing member 125 may not be required to seal tissue site 105. For example, tissue site 105 may be capable of being "self-sealed" to maintain reduced pressure. In the case of subcutaneous and deep tissue wounds, cavities, and fistulas, maintenance of reduced pressure at tissue site 105 may be possible without the use of sealing member 125. Since tissue often encases or surrounds these types of tissue sites, the tissue surrounding the tissue site acts effectively as a sealing member.

The reduced pressure generated by reduced pressure source 110 may be applied to tissue site 105 using source tube 130 and delivery tube 135. Source tube 130 and delivery tube 135 may be any tube through which a gas, liquid, gel, or other fluid may flow. For example, exudate from tissue site 105 may flow through delivery tube 135. In FIG. 1, source line 130 couples reduced pressure source 110 to canister 140 and delivery tube 135 couples canister 140 to dressing 115. However, in another embodiment, reduced pressure source 135 may be directly coupled to dressing 115 using delivery tube 135.

Source tube 130 and delivery tube 135 may be made from any material. Source tube 130 and delivery tube 135 may be either flexible or inflexible. Also, source tube 130 and delivery tube 135 may include one or more paths or lumens through which fluid may flow. For example, delivery tube 135 may include two lumens. In this example, one lumen may be used for the passage of exudate from tissue site 105 to canister 140. The other lumen may be used to deliver fluids, such as air, antibacterial agents, antiviral agents, cell-growth promotion agents, irrigation fluids, or other chemically active agents, to tissue site 105. The fluid source from which these fluids originate is not shown in FIG. 1. Additional details regarding the inclusion of multi-lumen tubes in reduced pressure treatment system 100 are provided below.

In one embodiment, delivery tube 135 is coupled to manifold 120 via connection member 145. Connection member 145 permits the passage of fluid from manifold 120 to delivery tube 135, and vice versa. For example, exudates collected from tissue site 105 using manifold 120 may enter delivery tube 135 via connection member 145. In another embodiment, reduced pressure treatment system 100 does not include connection member 145. In this embodiment, delivery tube 135 may be inserted directly into sealing member 125 or manifold 120 such that an end of delivery tube 135 is adjacent to or in contact with manifold 120.

Reduced pressure treatment system 100 includes canister 140. Liquid, such as exudate, from tissue site 105 may flow through delivery tube 135 into canister 140. Canister 115 may be any device or cavity capable of containing a fluid, such as gases and liquids, as well as fluids that contain solids. For example, canister 115 may contain exudates from tissue site 105. Source tube 130 and delivery tube 135 may be directly connected to canister 140, or may be coupled to canister 140 via a connector, such as connector 150.

The canister 140 may be a flexible or rigid canister, a bag, or pouch fluidly connected to manifold 120 by delivery tube 135. Canister 140 may be a separate container or may be operably combined with reduced pressure source 110 to collect exudate and fluids. In an illustrative embodiment in which a manual pump, such as a bellows pump, is used as reduced pressure source 110, the variable-volume chamber that generates the reduced pressure may also serve as canister 140, collecting fluid as the chamber expands. The canister 140 may include a single chamber for collecting fluids, or alternatively may include multiple chambers. A desiccant or absorptive material may be disposed within canister 140 to trap or control fluid once the fluid has been collected. In the absence of canister 140, a method for controlling exudate and other fluids may be employed in which the fluids, especially those that are water soluble, are allowed to evaporate from manifold 120.

Reduced pressure treatment system 100 includes pressure sensor 155. Pressure sensor 155 detects an actual reduced pressure at tissue site 105. In one non-limiting example, pressure sensor 155 is a silicon piezoresistive gauge pressure sensor. In one embodiment, pressure sensor 155 is the only pressure sensor included in reduced pressure treatment system 100. In this embodiment, reduced pressure treatment system 100 includes no other pressure sensor other than pressure sensor 155.

Pressure sensor 155 detects the reduced pressure at tissue site 105 via control tube 160. Control tube 160 is any tube through which a gas may flow. Control tube 160 may be made from any material. Control tube 160 may be either flexible or inflexible. Also, control tube 160 may include one or more paths or lumens through which fluid may flow.

In FIG. 1, control tube 160 is shown as passing through connector 150. However, the placement of control tube 160 may be varied to accommodate particular needs and applications. For example, control tube 160 may be routed through canister 140, along an outside surface of canister 140, or may bypass canister 140. The end of control tube 160 that is opposite of pressure sensor 155 may be coupled to manifold 120 via connector 145. In another example, control tube 160 may be inserted directly into sealing member 125 or manifold 120 such that an end of control tube 160 is adjacent to or in contact with manifold 120.

In another embodiment, delivery tube 135 and control tube 160 are each lumens in a single multi-lumen tube. Source tube 130 and control tube 160 may also each be lumens in a single multi-lumen tube. In the example in which reduced pressure source 110 is coupled to manifold 120 using only delivery tube 135, a single multi-lumen tube may be used to couple both reduced pressure source 110 and pressure sensor 155 to manifold 120. Additional details regarding the multi-lumen embodiments will be provided below in FIGS. 2 and 3.

Pressure sensor 155 may be located anywhere on reduced pressure treatment system 100. In FIG. 1, pressure sensor 155 is shown to be remote from tissue site 105. In this example, the reduced pressure at tissue site 105 may be detected from remotely located pressure sensor 155 through control tube 160, which permits the flow of gas. Also in this example, pressure sensor may be directly or indirectly coupled to other remotely located components of reduced pressure treatment system 100, such as reduced pressure source 110, canister 140, or any other illustrated component of reduced pressure treatment system 100. In another example, pressure sensor 155 may be placed adjacent to tissue site 155. In this example, pressure sensor 155 may not require the use of control tube 160 to detect the pressure at tissue site 105. In one non-limiting example, pressure sensor 155 is directly coupled to manifold 120 or placed between sealing member 125 and manifold 120.

Reduced pressure treatment system 100 includes control tube valve 165. Control tube valve 165 may be coupled to control tube 160. Control tube valve 165 may be any valve capable of relieving the reduced pressure in control tube 160. Non-limiting examples of control tube valve 165 include a pneumatic solenoid valve, a proportional valve, or a mechanical valve.

In one example, control tube valve 165 may be manually controlled by a human being. In another example, control tube valve 165 may be controlled by controller 170. In one embodiment, control tube valve 165 may be opened to relieve the reduced pressure in control tube 160 when a blockage is detected in control tube 160. Such a blockage may occur, for example, when exudate or other fluid from tissue site 105 clogs control tube 160. By relieving the reduced pressure in control tube 160 via control tube valve 165, the blockage may be cleared from control tube 160.

Reduced pressure treatment system 100 also includes relief valve 175. Relief valve 175 may be a valve that is coupled to any one of or any combination of source tube 130, canister 140, connector 150, delivery tube 135, connector 145, reduced pressure source 110, or dressing 115. Relief valve 175 may any type of valve capable of relieving the reduced pressure at tissue site 105. Non-limiting examples of relief valve 175 include a pneumatic solenoid valve, a proportional valve, or a mechanical valve. In one example, relief valve 175 may be opened to relieve the reduced pressure at tissue site 105. Relief valve 175 may also be used to manage the reduced pressure at tissue site 105. Additional details regarding the use of relief valve 175 and other components of the reduced pressure treatment system 100 to manage the reduced pressure at tissue site 105 are provided below.

Reduced pressure treatment system includes controller 170. Controller 170 is any device capable of processing data, such as data from pressure sensor 155. Controller 170 may also control the operation of one or more components of reduced pressure treatment system 100, such as reduced pressure source 110, relief valve 175, control tube valve 165, pressure sensor 155, or indicator 180. In one embodiment, controller 170 receives and processes data, such as data from pressure sensor 155, and controls the operation of one or more components of reduced pressure treatment system 100 to manage the reduced pressure at tissue site 105.

In one embodiment, controller 170 determines a target reduced pressure for tissue site 105. The target reduced pressure may be a user-definable reduced pressure for tissue site 105. The target reduced pressure may also be determined by controller 170. In one example, the target reduced pressure is a reduced pressure that provides an effective treatment of tissue site 105 and takes into account safety issues associated with applying reduced pressure to tissue site 105.

In one example, pressure sensor 155 detects the reduced pressure at tissue site 105. The reduced pressure measurement may be received by controller 170 from pressure sensor 155. Controller 170 may compare the reduced pressure received from pressure sensor 155 with the target reduced pressure to form a comparison. Controller 170 may then perform or direct a component of reduced pressure treatment system 100 to perform a reduced pressure management function based on the comparison.

In one embodiment, controller 170, in performing the reduced pressure management function based on the comparison, decreases a generated reduced pressure generated by reduced pressure source 110 in response to the actual reduced pressure exceeding the target reduced pressure. For example, if reduced pressure source 110 is a motorized or otherwise electrically operated reduced pressure source, the motor or electrical process may be slowed such that reduced pressure source 110 generates a decreased amount of reduced pressure. In another non-limiting example, if reduced pressure source 110 is a chemically driven reduced pressure source, the chemical process driving reduced pressure source 110 may be slowed or altered to decrease the amount of reduced pressure generated by reduced pressure source 110.

In another embodiment, controller 170 opens relief valve 175 to decrease the reduced pressure at tissue site 105 in response to the actual reduced pressure, as measured by pressure sensor 155, exceeding the target reduced pressure by a predetermined threshold. The predetermined threshold may be determined by a user or by a component of reduced pressure treatment system 100, such as controller 170. In one example, the predetermined threshold is a threshold that helps to ensure the safety of tissue at tissue site 105. For example, the predetermined threshold may be determined such that an actual reduced pressure at tissue site 105 that exceeds the target reduced pressure by the predetermined threshold may affect the safety of tissue at tissue site 105. Thus, this embodiment may be implemented as a safety mechanism using the single pressure sensor 155.

In another embodiment, controller 170 turns off or shuts down reduced pressure source 110 in response to the actual reduced pressure, as measured by pressure sensor 155, exceeding the target reduced pressure by a predetermined threshold. Turning off or shutting down reduced pressure source 110 decreases the reduced pressure at tissue site 105. In one example, the predetermined threshold beyond which reduced pressure source 110 is turned off is greater than or less than the predetermined threshold beyond which relief valve 175 is opened as described in the previous embodiment. Thus, in this example, a two-tiered safety mechanism is employed to ensure the safety of tissue at tissue site 105. In another example, the predetermined threshold beyond which reduced pressure source 110 is turned off is the same as the predetermined threshold beyond which relief valve 175 is opened.

In another example, controller 170, in performing the reduced pressure management function based on the comparison, increases a generated reduced pressure generated by reduced pressure source 110. For example, if reduced pressure source 110 is a motorized or otherwise electrically operated reduced pressure source, the pace of the motor or electrical process may be increased such that reduced pressure source 110 generates an increased amount of reduced pressure. In another non-limiting example, if reduced pressure source 110 is a chemically driven reduced pressure source, the chemical process driving reduced pressure source 110 may be hastened or altered to increase the amount of reduced pressure generated by reduced pressure source 110.

In another embodiment, controller 170 determines a responsiveness of the actual reduced pressure at tissue site 105, as measured by pressure sensor 155, to an increase in the generated reduced pressure from reduced pressure source 110. In one example, controller 170 may detect when the reduced pressure generated by reduced pressure source is increased or decreased. For example, controller 170 may be able to detect when the motor speed, chemical reaction speed, or compression speed of reduced pressure source 110 has increased or decreased. Other parameters that may be detected by controller 170 to determine such an increase or decrease include the current draw of a motor, which may indicate the pump's duty. The level of power or pulse-width modulation required to be given to the motor to deliver the required reduced pressure to tissue site 105 may also be detected. Controller 170 may also be able to infer that the reduced pressure generated by reduced pressure source is increased or decreased based on the comparison between the actual reduced pressure measured by pressure sensor 155 and the target reduced pressure.

In one embodiment, controller 170 directs indicator 180 to emit a signal in response to the actual reduced pressure at tissue site 105, as measured by pressure sensor 155, being nonresponsive to increasing the generated reduced pressure. In one embodiment, indicator 180 is a light emitting diode, or "LED." In this embodiment, indicator 180 illuminates in response to the actual reduced pressure at tissue site 105 being nonresponsive to increasing the generated reduced pressure.

In another embodiment, indicator 180 is a sound emitting device, such as a speaker. In this embodiment, indicator 180 emits a sound in response to the actual reduced pressure at tissue site 105 being nonresponsive to increasing the generated reduced pressure.

In another embodiment, the actual reduced pressure at tissue site 105 is nonresponsive to increasing the generated reduced pressure when the actual reduced pressure at tissue site 105 fails to increase within a predefined time period in response to increasing the generated reduced pressure. Such nonresponsiveness may indicate that one or more components of reduced pressured treatment system 100, such as delivery tube 135 or source tube 130, are blocked or have a leak. For example, liquid, such as exudate, from tissue site 105 may have clogged delivery tube 135 or source tube 130. In another example, a rupture may have occurred at a location along delivery tube 135 or source tube 130.

The predefined time period may be any time period, and may be set by a user of reduced pressure treatment system 100, or a component of reduced pressure treatment system 100, such as controller 170. In one example, the predefined time period in a range of one second to ten seconds or four seconds to six seconds. In one specific non-limiting example, the predefined time period is five seconds.

In another embodiment, the actual reduced pressure at tissue site 105 is nonresponsive to increasing the generated reduced pressure when the actual reduced pressure at tissue site 105 fails to meet a target reduced pressure within a predefined time period in response to increasing the generated reduced pressure. Similar to the previously described embodiment, such nonresponsiveness may indicate that one or more components of reduced pressured treatment system 100, such as delivery tube 135 or source tube 130, are blocked or have a leak.

In another embodiment of the present invention, if reduced pressure source 110 is a vacuum pump and motor, a sensor may be coupled to the vacuum pump or motor to measure the pump or motor speed. The measurements acquired by the sensor may be used to infer the pressure delivered by the pump, thereby providing a mechanism for determining whether leaks or blockages are present and distinguishing between them. For example, detection of leaks may be performed by monitoring the speed of either or both of the pump or motor. If a leak occurs while reduced pressure treatment is being administered, either or both of the pump speed or motor speed will likely increase indicating that the pump is generating more reduced pressure. If a blockage occurs, the speed of either or both of the pump or motor will likely decrease. The output from the pump or motor speed sensor may be used by controller 170 to emit a signal using indicator 180 during a leak or blockage condition.

In one specific illustrative example, reduced pressure source 110 includes a motor having a speed. In this example, a sensor may detect the speed of the motor. Indicator 180 may emit a signal when the speed of the motor changes by a threshold amount. The threshold amount may be any amount, and may be set by a user of reduced pressure treatment system 100, or a component of reduced pressure treatment system 100, such as controller 170. The threshold amount may be expressed in terms of a finite quantity, a percentage, or any combination thereof.

Figure 2:
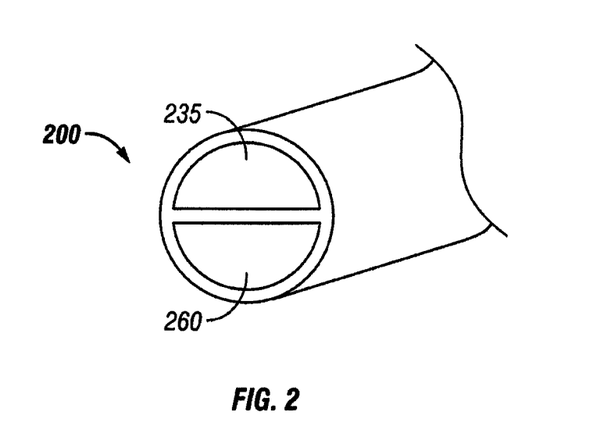
FIG. 2 is a perspective view of a multi-lumen tube in accordance with an illustrative embodiment of the present invention.

Turning now to FIG. 2, a perspective view of a multi-lumen tube is depicted in accordance with an illustrative embodiment of the present invention. Specifically, FIG. 2 depicts multi-lumen tube 200, which may be implemented in a reduced pressure treatment system, such as reduced pressure treatment system 100 in FIG. 1.

Multi-lumen tube 200 includes two lumens. Specifically, multi-lumen tube 200 includes lumens 235 and 260. Although multi-lumen tube 200 includes two lumens 235 and 160, multi-lumen tube may have any number of lumens, such as three, four, or ten.

In one embodiment, one of lumens 235 and 260, such as lumen 235, is a delivery tube or source tube, such as delivery tube 135 and source tube 130 in FIG. 1. In another embodiment, one of lumens 235 and 260, such as lumen 260, is a control tube, such as control tube 160 in FIG. 1. By incorporating a combination of a delivery tube, source tube, and control tube as lumens in a single multi-lumen tube, the number of separate tubes included in the reduced pressure treatment system may be reduced. The reduced number of tubes simplifies the reduced pressure treatment system for use by a user, and lessens the burden of carrying the reduced pressure treatment system.

Figure 3:
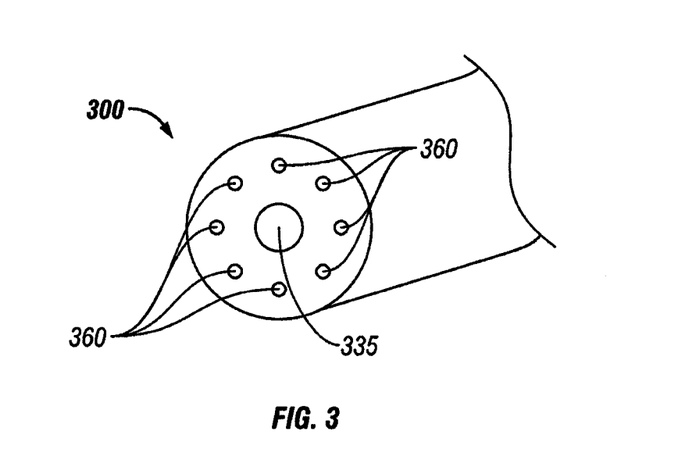
FIG. 3 is a perspective view of a multi-lumen tube in accordance with an illustrative embodiment of the present invention.

Turning now to FIG. 3, a perspective view of a multi-lumen tube is depicted in accordance with an illustrative embodiment of the present invention. Specifically, FIG. 3 depicts multi-lumen tube 300, which may be implemented in a reduced pressure treatment system, such as reduced pressure treatment system 100 in FIG. 1. Multi-lumen tube 300 may be a non-limiting example of multi-lumen tube 200 in FIG. 2.

Multi-lumen tube 300 includes nine lumens. Specifically, multi-lumen tube 300 includes lumen 335 and peripheral lumens 360. Although multi-lumen tube 300 shows peripheral lumens 360 as encircling lumen 335, the lumens in multi-lumen tube 300 may have any spatial configuration relative to one another.

In one embodiment, one of lumens 335 and 360, such as lumen 335, is a delivery tube or source tube, such as delivery tube 135 and source tube 130 in FIG. 1. In another embodiment, one of lumens 335 and 360, such as any or all of lumens 360, is a control tube, such as control tube 160 in FIG. 1. Similar to multi-lumen tube 300 in FIG. 3, by incorporating any combination of a delivery tube, source tube, and control tube as lumens in multi-lumen tube 300, the number of separate tubes included in the reduced pressure treatment system may be reduced to increase the usability of the reduced pressure treatment system in which the multi-lumen tube is included.

Figure 4:
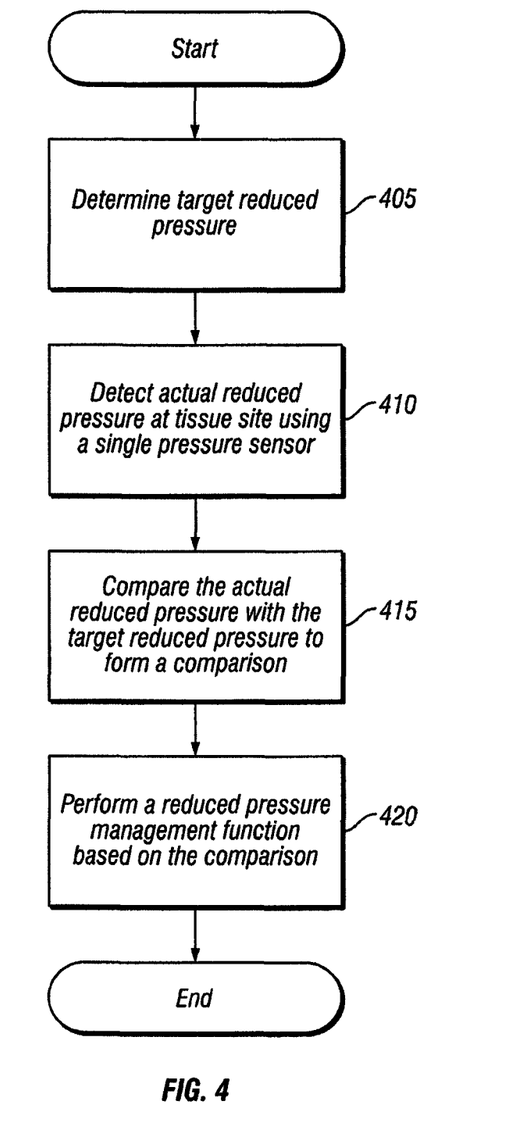
FIG. 4 is a flowchart illustrating a process for managing reduced pressure at a tissue site in accordance with an illustrative embodiment of the present invention.

Turning now to FIG. 4, a flowchart illustrating a process for managing reduced pressure at a tissue site is depicted in accordance with an illustrative embodiment of the present invention. The process illustrated in FIG. 4 may be implemented by a controller, such as controller 170 in FIG. 1, in conjunction with other components of a reduced pressure treatment system, such as components of reduced pressure treatment system 100 in FIG. 1.

The process begins by determining a target reduced pressure (step 405). The process detects an actual reduced pressure at a tissue site using a single pressure sensor (step 410). The process compares the actual reduced pressure with the target reduced pressure to form a comparison (step 415). The process performs a reduced pressure management function based on the comparison (step 420).

Figure 5:
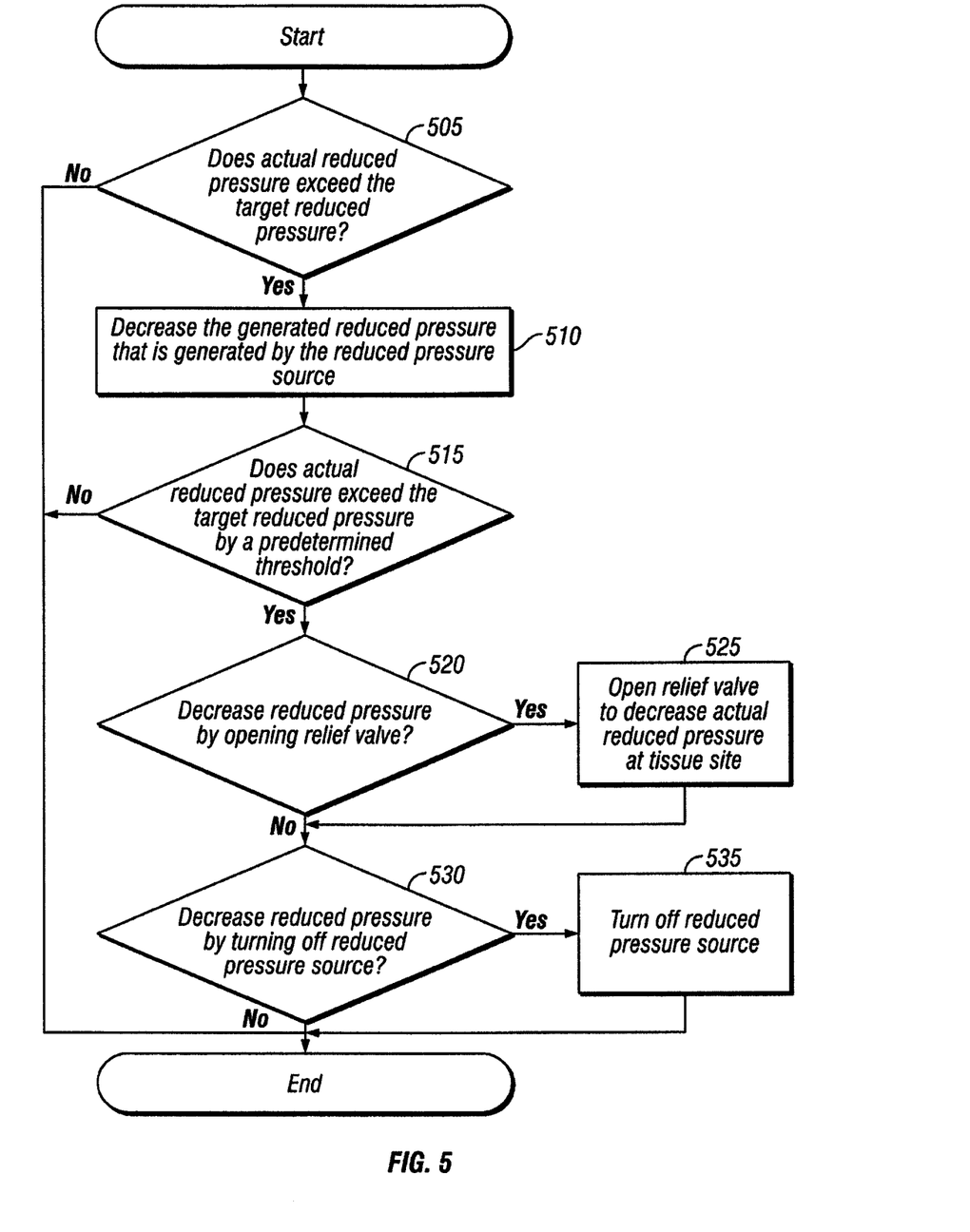
FIG. 5 is a flowchart illustrating a process for managing reduced pressure at a tissue site in accordance with an illustrative embodiment of the present invention.

Turning now to FIG. 5, a flowchart illustrating a process for managing reduced pressure at a tissue site is depicted in accordance with an illustrative embodiment of the present invention. The process illustrated in FIG. 5 may be implemented by a controller, such as controller 170 in FIG. 1, in conjunction with other components of a reduced pressure treatment system, such as components of reduced pressure treatment system 100 in FIG. 1. The process illustrated in FIG. 5 provides illustrative embodiments and additional detail with respect to steps 415 and 420 in FIG. 4.

The process begins by determining whether the actual reduced pressure exceeds the target reduced pressure (step 505). If the process determines that the actual reduced pressure does not exceed the target reduced pressure, the process terminates. Returning to step 505, if the process determines the actual reduced pressure exceeds the target reduced pressure, the process decreases the generated reduced pressure that is generated by the reduced pressure source (step 510).

The process determines whether the actual reduced pressure exceeds the target reduced pressure by a predetermined threshold (step 515). If the process determines that the actual reduced pressure does not exceed the target reduced pressure by the predetermined threshold, the process terminates. Returning to step 515, if the process determines that the actual reduced pressure exceeds the target reduced pressure by a predetermined threshold, the process determines whether to decrease the reduced pressure by opening a relief valve (step 520). If the process determines to decrease the reduced pressure by opening a relief valve, the process opens the relief valve to decrease the actual reduced pressure at the tissue site (step 525).

Returning to step 520, if the process determines not to decrease the reduced pressure by opening a relief valve, the process determines whether to decrease the reduced pressure by turning off the reduced pressure source (step 530). If the process determines to decrease the reduced pressure by turning off the reduced pressure source, the process turns off the reduced pressure source (step 535). The process then terminates. Returning to step 530, if the process determines not to decrease the reduced pressure by turning off the reduced pressure source, the process terminates.

Figure 6:
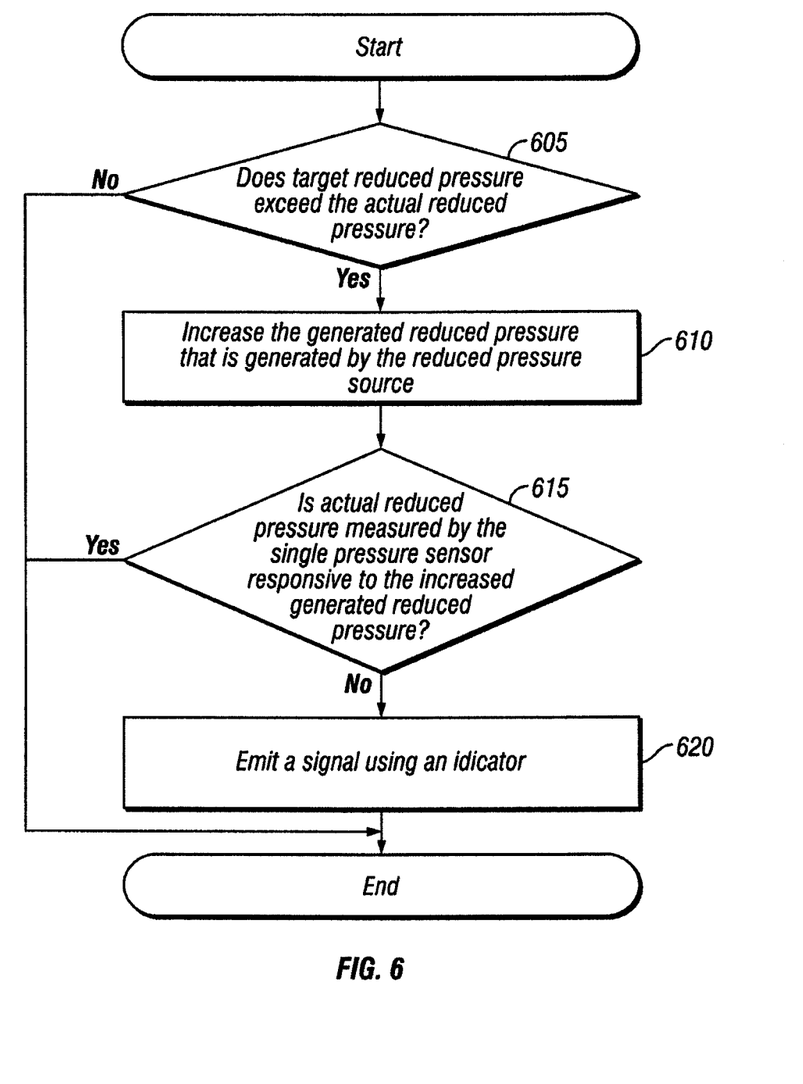
FIG. 6 is a flowchart illustrating a process for managing reduced pressure at a tissue site in accordance with an illustrative embodiment of the present invention.

Turning to FIG. 6, a flowchart illustrating a process for managing reduced pressure at a tissue site is depicted in accordance with an illustrative embodiment of the present invention. The process illustrated in FIG. 6 may be implemented by a controller, such as controller 170 in FIG. 1, in conjunction with other components of a reduced pressure treatment system, such as components of reduced pressure treatment system 100 in FIG. 1. The process illustrated in FIG. 5 provides illustrative embodiments and additional detail with respect to steps 415 and 420 in FIG. 4.

The process begins by determining whether the target reduced pressure exceeds the actual reduced pressure (step 605). If the process determines that the target reduced pressure does not exceed the actual reduced pressure, the process terminates. Returning to step 605, if the process determines that the target reduced pressure exceeds the actual reduced pressure, the process increases the generated reduced pressure that is generated by the reduced pressure source (step 610).

The process determines whether the actual reduced pressure measured by the single pressure sensor is responsive to the increased generated reduced pressure (step 615). If the process determines that the actual reduced pressure measured by the single pressure sensor is responsive to the increased generated reduced pressure, the process terminates. Returning to step 615, if the process determines that the actual reduced pressure measured by the single pressure sensor is nonresponsive to the increased generated reduced pressure, the process emits a signal using an indicator (step 620). The process then terminates.

Figure 7:
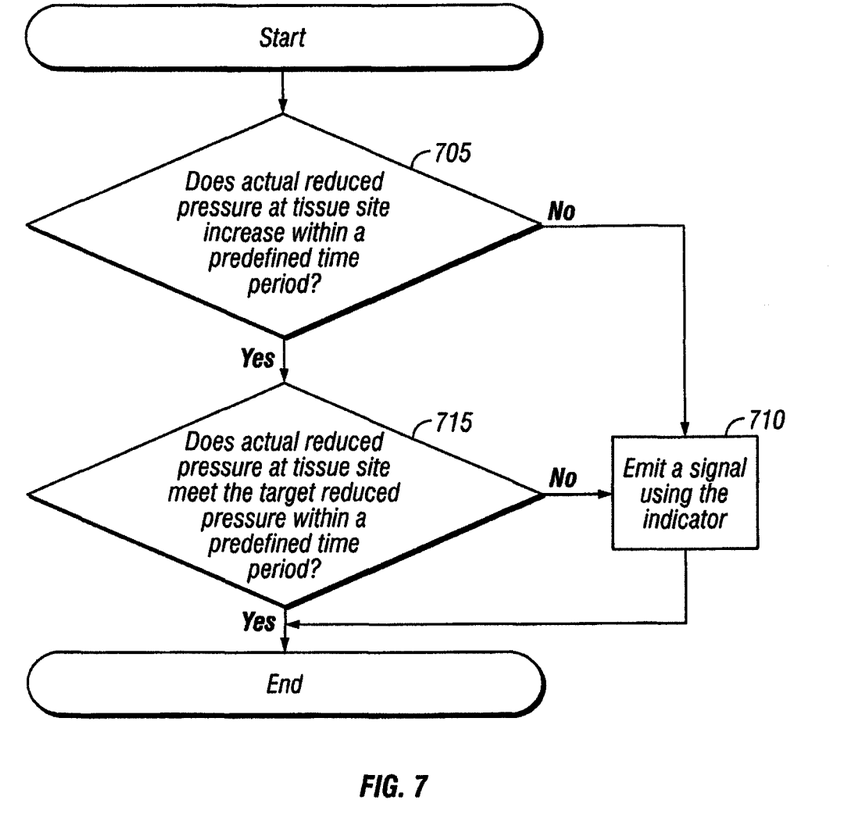
FIG. 7 is a flowchart illustrating a process for managing reduced pressure at a tissue site in accordance with an illustrative embodiment of the present invention.

Turning now to FIG. 7, a flowchart illustrating a process for managing reduced pressure at a tissue site is depicted in accordance with an illustrative embodiment of the present invention. The process illustrated in FIG. 7 may be implemented by a controller, such as controller 170 in FIG. 1, in conjunction with other components of a reduced pressure treatment system, such as components of reduced pressure treatment system 100 in FIG. 1. The process illustrated in FIG. 7 provides illustrative embodiments and additional detail with respect to steps 615 and 620 in FIG. 6.

The process begins by determining whether the actual reduced pressure at the tissue site increases within a predefined time period (step 705). If the process determines that the actual reduced pressure at the tissue site does not increase within a predefined time period, the process emits a signal using an indicator (step 710). The process then terminates.

Returning to step 705, if the process determines that the actual reduced pressure at the tissue site increases within a predefined time period, the process determines whether the actual reduced pressure at the tissue site meets the target reduced pressure within a predefined time period (step 715). If the process determines that the actual reduced pressure at the tissue site does not meet the target reduced pressure within a predefined time period, the process emits a signal using the indicator (step 710). The process then terminates. Returning to step 715, if the process determines that the actual reduced pressure at the tissue site meets the target reduced pressure within a predefined time period, the process then terminates.

The flowcharts and block diagrams in the different depicted embodiments illustrate the architecture, functionality, and operation of some possible implementations of the apparatus and methods. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

The illustrative embodiments may be configured to be a light weight and low cost system that consumes less power than currently used reduced pressure treatment systems. The reductions in size and weight are particularly important when the system is to be used to treat low-severity wounds and wounds on ambulatory patients. These wounds and patients require a system that is unobtrusive and lightweight so that discomfort to the patient and hindrance of movement are minimized.

One way in which cost, weight, and power consumption are minimized is through the use of only one sensor to measure pressure. As previously mentioned, traditional systems typically use two pressure sensors, one to measure pressure at the tissue site and one to measure pressure at the reduced pressure source. However, the elimination of the pressure sensor measuring pressure at the reduced pressure source allows significant reductions in the amount of electronic circuitry required and also the amount of power consumed by the system. Additionally, any circuitry and software used to compare the two sensor readings is eliminated. In addition, the illustrative embodiments enable the application of a predefined reduced pressure to tissue, while providing detection and notification of certain anomalous system conditions with fewer components than prior systems.

The illustrative embodiments also eliminate the need to approximate the tissue site pressure using a measured value at the reduced pressure source. Further, determining the pressure directly at the tissue site, when included with the other features of the illustrative embodiments, allows the reduced pressure treatment system to detect leaks and blockages by observing pressure changes at the tissue site in response to operational changes made at the reduced pressure source.

We claim:

1. A method for managing reduced pressure at a tissue site, the method comprising:
   detecting a change to an operating parameter of a reduced pressure source indicative of a change to reduced pressure generated by the reduced pressure source;
   determining an actual reduced pressure at the tissue site using a single pressure sensor; and
   responsive to the actual reduced pressure at the tissue site being nonresponsive to the change to the operating parameter, emitting a signal using an indicator.

2. The method of claim 1, wherein the actual reduced pressure at the tissue site is nonresponsive to increasing the generated reduced pressure when the actual reduced pressure at the tissue site fails to increase within a predefined time period in response to increasing the generated reduced pressure.

3. The method of claim 1, wherein the actual reduced pressure at the tissue site is nonresponsive to increasing the generated reduced pressure when the actual reduced pressure at the tissue site fails to meet a target reduced pressure within a predefined time period in response to increasing the generated reduced pressure.

4. The method of claim 1, further comprising:
   determining a target reduced pressure for the tissue site; and
   comparing the actual reduced pressure detected by the single pressure sensor with the target reduced pressure.

5. The method of claim 4, further comprising:
   responsive to the actual reduced pressure exceeding the target reduced pressure, decreasing the generated reduced pressure generated by the reduced pressure source.

6. The method of claim 1, wherein the responsiveness is determined by monitoring whether the actual reduced pressure at the tissue site changes within a predefined period of time.

7. The method of claim 1, wherein the responsiveness is determined by monitoring whether the actual reduced pressure at the tissue site meets a target reduced pressure within a predefined period of time.

8. The method of claim 1, wherein the operating parameter is a current draw by a motor associated with the reduced pressure source.

9. The method of claim 1, wherein the operating parameter is a speed of a motor associated with the reduced pressure source.

10. The method of claim 1, wherein the operating parameter is a speed of a chemical reaction associated with the reduced pressure source.

11. The method of claim 1, wherein the responsiveness is determined by monitoring whether the actual reduced pressure at the tissue site changes within a range of 1 to 10 seconds.

12. The method of claim 1, wherein the responsiveness is determined by monitoring whether the actual reduced pressure at the tissue site changes within a range of 4 to 6 seconds.

* * * * *